United States Patent
Herr et al.

(10) Patent No.: US 7,795,364 B2
(45) Date of Patent: Sep. 14, 2010

(54) POLYMERIC PHOTOINITIATORS

(75) Inventors: Donald E. Herr, Doylestown, PA (US); Ziyi Hu, Somerville, NJ (US); Charles W. Paul, Madison, NJ (US); Robert W. R. Humphreys, Annandale, NJ (US)

(73) Assignee: Henkel AG & Co. KGaA, Duesseldorf (DE)

( * ) Notice: Subject to any disclaimer, the term of this patent is extended or adjusted under 35 U.S.C. 154(b) by 797 days.

(21) Appl. No.: 11/606,685

(22) Filed: Nov. 30, 2006

(65) Prior Publication Data

US 2007/0208099 A1    Sep. 6, 2007

Related U.S. Application Data

(62) Division of application No. 10/465,473, filed on Jun. 18, 2003, now Pat. No. 7,157,535.

(60) Provisional application No. 60/389,972, filed on Jun. 19, 2002.

(51) Int. Cl.
  *C08F 36/02* (2006.01)
  *G03C 1/00* (2006.01)

(52) U.S. Cl. .................... 526/335; 526/286; 430/281.1; 430/913; 430/286.1

(58) Field of Classification Search ................ 526/316, 526/303.1, 307.2, 266, 318.1, 307.6, 307.7, 526/335, 286; 430/281.1, 913, 283.1
See application file for complete search history.

(56) References Cited

U.S. PATENT DOCUMENTS

| | | | |
|---|---|---|---|
| 3,903,322 A | 9/1975 | Ravve et al. | |
| 4,207,156 A | 6/1980 | Collins et al. | |
| 5,512,606 A * | 4/1996 | Allen et al. | 522/48 |
| 5,773,485 A | 6/1998 | Bennett et al. | |
| 5,776,658 A | 7/1998 | Niesert et al. | |

FOREIGN PATENT DOCUMENTS

| | | |
|---|---|---|
| DE | 195 01 025 A1 * | 7/1996 |
| EP | 0192167 | 8/1986 |
| EP | 0705865 | 4/1996 |
| JP | 08157510 | 6/1996 |
| WO | WO 88/01281 | 2/1988 |
| WO | WO 88/09800 | 12/1988 |
| WO | WO 95/10552 | 4/1995 |

OTHER PUBLICATIONS

Allen et al., Journal of Photochemistry and photobiology A: Chemistry, 99, 191-196 (1996).*
Allen et al., Journal of Photochemistry and Photobiology A: Chemistry, 102, 253-258(1997).*
Allen et al., Eur. Polym. J., 31(1), 15-21(1995).*
Allen et al., Polymer, 36(24), 4665-4674(1995).*
Catalina et al., Polymer, 42, 1825-1832 (2001).*
Pullen et al., Eur. Polym. J., 32(8), 943-955(1996).*
David, et al., Polymer, 1969, 10, pp. 21-27.
Gu, et al., Adv. Functional Materials, 2005, 15(1), pp. 125-130.
Carlini, et al., Radiation Curing in Science and Technology, Elsevier Appl. Sci., 1993, 2, pp. 283-321.
European Search Report issued for European Patent Application No. EP 08020646 dated Apr. 23, 2009.
European Search Report issued for European Patent Application No. EP 08020647 dated Apr. 1, 2009.

* cited by examiner

*Primary Examiner*—Ling-Siu Choi
(74) *Attorney, Agent, or Firm*—Steven C. Bauman; James E. Piotrowski

(57) ABSTRACT

UV curable compositions, polymeric photoinitiators and precursors therefor are described.

11 Claims, 2 Drawing Sheets

POLYMERIC PHOTOINITIATORS

Figure 1:
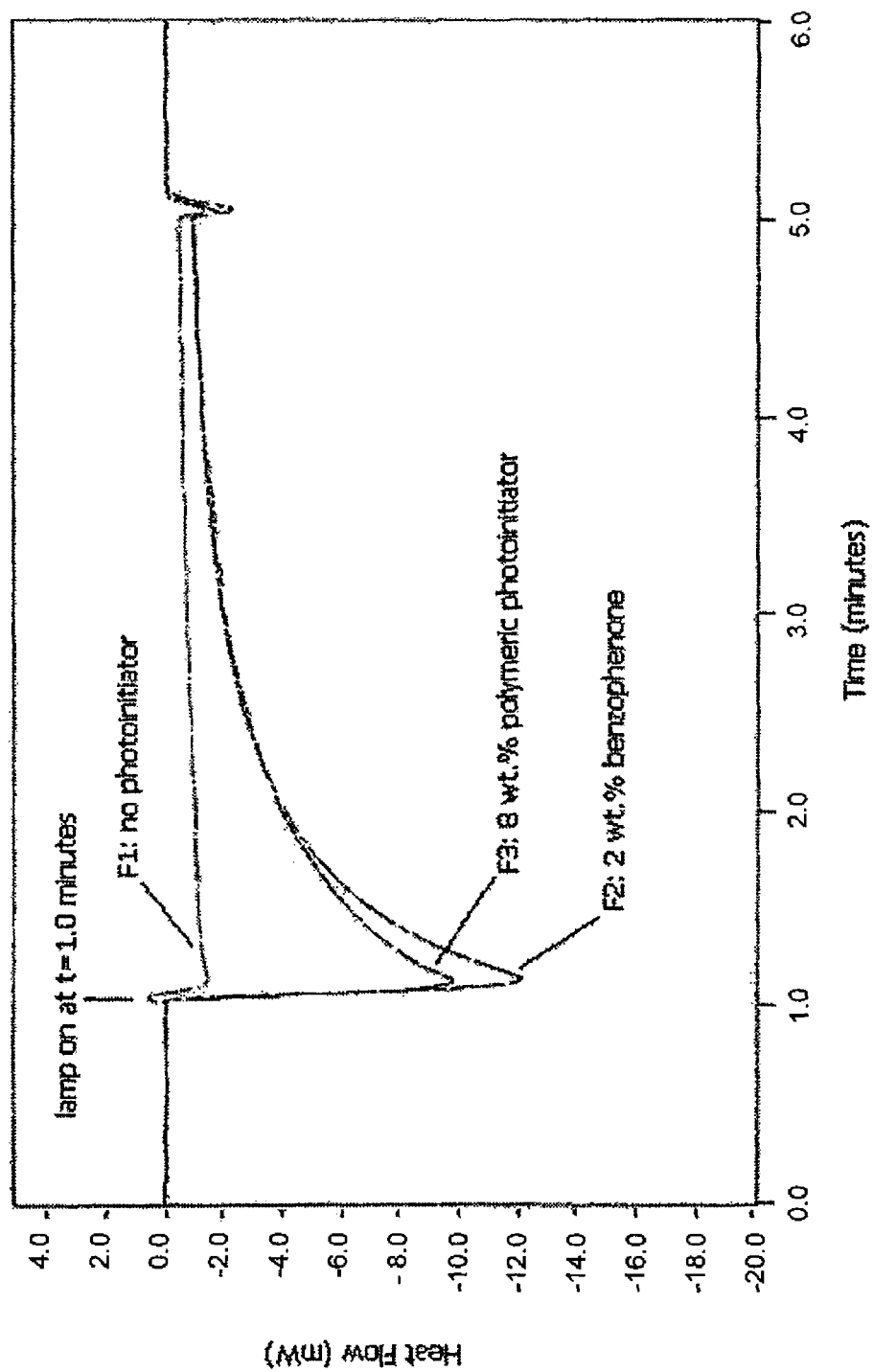

This is a divisional of U.S. application Ser. No. 10/465,473, filed Jun. 18, 2003, now U.S. Pat. No. 7,157,535 which application claims the benefit of the earlier Jun. 19, 2002 filing date of U.S. provisional application No. 60/389,972.

FIELD OF THE INVENTION

The invention relates to polymeric photoinitiator compositions, precursors useful in the preparation of such polymeric photoinitiators and to the use of these polymers in, e.g., UV curable adhesives, UV curable coating compositions and UV curable encapsulants.

BACKGROUND OF THE INVENTION

The primary function of a photoinitiator is to generate polymerization initiating radicals when the photoinitiator is irradiated with ultraviolet (UV) light. Photoinitiators are classified into "Type I" (or photocleavage) photoinitiators and "Type II" (or H-abstraction) photoinitiators according to the pathways by which the effective initiating radicals are generated.

In contrast to photocleavage photoinitiators which are decomposed by UV light directly into radicals which are effective in initiating polymerization, H-abstraction photoinitiators require a hydrogen donor, or more generally a source of abstractable hydrogens in order to generate radicals that are effective in initiating polymerization. The process of H-abstraction is usually a bimolecular reaction requiring the encounter of a photoinitiator and a hydrogen-donor. Any source of abstractable hydrogens may be useful (e.g., any structure that yields a stable radical after H-abstraction may serve as a "H donor") and such sources include amines, thiols, unsaturated rubbers such as polybutadiene or polyisoprene, and alcohols.

The basic photochemistry and photophysics of both α-cleavage (Type I) and H-abstraction (Type II) photoinitiators has been well studied and utilized industrially in UV curable systems (see (a) Cowan, D. O.; Drisko, R. L. *Elements of Organic Photochemistry,* 1976, Plenum Press, chapters 3 and 4. (b) Turro, N. J. *Modern Molecular Photochemistry,* 1991, University Science Books, chapters 7, 10, and 13.). One well recognized problem with the use of UV curable systems for coating and adhesive applications is the fate of the photo-by products created by the curing process. In the case of typical α-cleavage type photoinitiators, the production of benzaldehyde (and often related compounds) is often a significant concern from both a toxicity and product odor standpoint. Such concerns become especially important when the use of radiation curable materials is considered for applications that involve skin or food contact. Various effective approaches have been taken to reduce the odor and extractable by-product content of UV curable materials. One approach has been the use of copolymerizable or polymeric photoinitiators which are chemically incorporated into the cured polymeric matrix as opposed to remaining in the irradiated material as a small molecule (see (a) Fouassier, J. P.; Rabek, J. F., Eds. *Radiation Curing in Science and Technology,* 1993, Elsevier Appl. Sci., vol. 2, 283-321. (b) Fouassier, J. P. *Photoinitiation, Photopolymerization and Photocuring, Fundamentals and Applications,* 1995, Hanser Publishers, 71-73.). Unfortunately, when utilizing α-cleavage photoinitiators at least one of the cleavage by-products still remains as a small molecule even if the other fragment is incorporated into a polymeric component of the system. Thus, although extractable and odorous by-products can be reduced through the use of polymeric or polymerizable Type I photoinitiators, they are not eliminated entirely.

The use of polymerizable or polymeric H-abstraction type photoinitiators, in principle, presents the possibility of creating a system with zero extractable components related to the photoinitiation system. Various groups have presented systems based upon poly(vinyl benzophenone) and its copolymers or polymers derived from acrylated benzophenone derivatives (see (a) David, C.; Demarteu, W.; Geuskens, G. *Polymer,* 1969, 10, 21-27. (b) Carlini, C.; Ciardelli, F.; Donati, D.; Gurzoni, F. *Polymer,* 1983, 24, 599-606.). The direct use of acrylated benzophenones has also been disclosed (U.S. Pat. No. 3,429,852). Unfortunately, these Type II systems often suffer from issues related to photoefficiency relative to analogous small molecule photoinitation systems.

It is notable that, in products requiring very low extractable levels or odor, any copolymerizable photoinitiator that does not fully react into the growing polymer network will remain in the final product as a small molecule, creating many of the same problems that photoinitiator fragments introduce. Thus, it is often most desirable to use polymeric photoinitiators as opposed to polymerizable photoinitiators. A key practical issue when utilizing polymeric photoinitiators is their compatibility with the resins systems in which they are to be used. An additional requirement of such polymeric photoinitiators, particularly those intended for use in hot melt adhesives and coatings, is that that they be thermally stable at the application temperature. The polymeric Type II photoinitiators known in the prior art fail to meet one or more of the requirements and needs noted above.

There continues to be a need in the art for improved H-abstraction photoinitiators useful in the manufacture of radiation curable adhesives and coating formulations. In particular, polymer-bound H-abstraction photoinitiators are needed to produce low odor products with fewer (or no) inherent extractable photochemical by-products. The current invention fulfils this need.

SUMMARY OF THE INVENTION

One aspect of the invention is directed to precursor compounds useful in the preparation of H-abstraction class photoinitiators, in particular polymeric H-abstraction class photoinitiators, more specifically rubber bound H-abstraction class photoinitiators. In a preferred embodiment the precursor is a SiH-functional benzophenone derivative which may be used in the preparation of polymeric benzophenone photoinitiators.

Another aspect of the invention is directed to rubber-bound polymeric H-abstraction class photoinitiators. In one embodiment the rubber-bound polymeric H-abstraction class photoinitiator is a styrene-butadiene-styrene (SBS)-bound polymeric H-abstraction class photoinitiator. In a particularly preferred embodiment the rubber-bound polymeric H-abstraction class photoinitiator is a poly(butadiene)-bound polymeric H-abstraction class photoinitiator. Both amide-linked, sulfide-linked, and silane-linked polymeric H-abstraction photoinitiator compositions are encompassed by the invention.

Still another aspect of the invention is directed to UV curable compositions comprising a polymeric H-abstraction photoinitiator. In a preferred embodiment the UV composition is a UV curable hot melt pressure sensitive adhesive. Adhesive and coating formulations based on, but not limited to, rubber, thiol-ene, maleimide and acrylate base resins are encompassed. A particularly preferred adhesive is a SBS or SIS rubber-based UV curable pressure sensitive adhesive comprising a poly(butadiene)-bound polymeric H-abstraction class photoinitiator.

Yet another aspect of the invention is directed to radiation cured hot melt pressure sensitive adhesives and radiation cured coating compositions, and to articles of manufacture comprising the cured adhesive and/or coating compositions.

A further aspect of the invention is directed to the use of the novel polymer-bound photoinitiators in UV curable coatings and adhesives in the same manner which small molecule Type II photoinitiators are often used. Preferred applications include thiol-ene, acrylate and maleimide based UV curable compositions.

BRIEF DESCRIPTION OF THE DRAWING FIGURES

Figure 2:
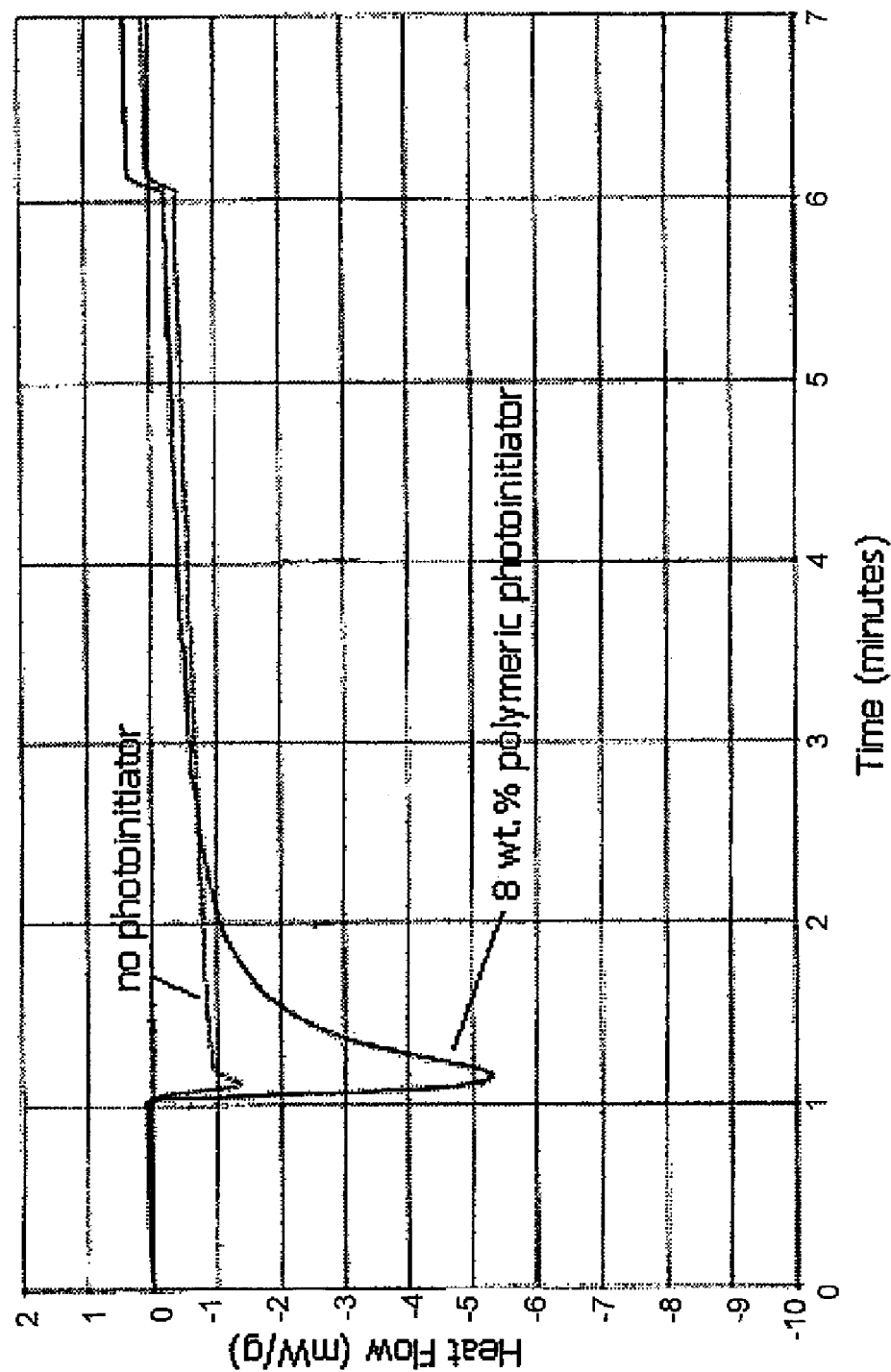

FIG. 1 shows the photoDSC analysis of a thiol-ene photopolymerization with and without the polymeric photoinitiator of the invention FIG. 2 shows the photoDSC analysis (300 nm cutoff filter) of a thiol-ene photopolymerization with and without the polymeric photoinitiator of the invention.

DETAILED DESCRIPTION OF THE INVENTION

All documents cited herein are incorporated in their entireties by reference.

The current invention provides polymeric H-abstraction class photoinitiators, in particular rubber-bound H-abstraction photoinitiator compositions, and adhesives, coating compositions and the like comprising such polymeric photoinitiators.

The polymeric H-abstraction class photoinitiators of the invention are prepared from precursors comprising a chromophore linked through a spacer unit to a functional group. Silane-functional, mercaptan-functional and amine-functional chromophores are encompassed. The unit between the functional group and the chromophore can be any organic moiety, preferably straight and branched chain alkyl or aryl, possibly including (but not limited to) heteroatoms such as O, S, N and Si. The spacer unit can also possess pendant heteroatom-containing substituents such as, but not limited to, alkoxy, mercaptoalkyl, amino and alkylamino. These functional precursors are subsequently covalently attached to unsaturated small molecules or polymers to produce the inventive polymeric photoinitiator molecules.

The functionalized chromophores of the invention are attached to small molecules or polymers that contain groups that are reactive with the functional group present on the chromophore.

Small molecules are defined are being non-polymeric materials. For example, SiH-functional chromophores may be reacted via a hydrosilation reaction with unsaturated small molecules such as bisphenol A diallyl ether, trimethylolpropane triallyl ether or multifunctional vinyl ethers such as cyclohexanedimethylol divinyl ether to form small molecule photoinitiators. These may be mono- or multifunctional depending on the choice of unsaturated small molecule.

As previously noted herein, it is often preferable/advantageous to graft one or more of the functional chromophores to a polymeric material to produce a polymeric photoinitiator. For example, SiH-functional chromophores may be grafted through hydrosilation to an unsaturated polymer such as poly (butadiene). The resulting polymeric photoinitiators will often contain more than one covalently linked chromophore per polymer chain, and the average number of chromophores per chain can be controlled through stoichiometry. In cases where the polymeric photoinitiator may also participate in UV crosslinking reactions as well as acting as a photoinitiator, it is often preferable that the polymeric photoinitiator contain more than two chromophore groups.

The light absorbing chromophores used in the photoinitiator system of the invention are chosen to match as closely as possible the emission bands of the light source. Useful chromophores include compounds which undergo H-abstraction photochemistry including but not limited to benzophenone and related aromatic ketones such as xanthone, thioxanthone, 4,4'-bis(N,N'-dimethylamino)benzophenone, benzil, quinones, quinoline, anthroquinone, fluorene, acetophenone, xanthone, phenanthrene and fluorenone. A reasonably comprehensive list of useful chromophores and photophysical data for such can be found in the *Polymer Handbook*, Brandrup J.; Immergut, E. H.; Grulke, E. A.; Eds., John Wiley & Sons, Inc., II/169, "Photopolymerization Reactions", Fouassier, J. P.; 1999.

Preferred SiH-functional chromophores for use in the practice of the invention are SiH-functional diarylketone having the following structure:

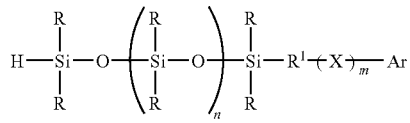

wherein

Ar is an aryl ketone moeity,

R is independently a linear or branched alkyl group, cycloalkyl, alkylenoxy, alkenyl or aryl group, an alkyl group containing a heteroatom, or H, $R^1$ is independently a linear or branched alkyl group, cycloalkyl, alkylenoxy, alkenyl or aryl group, or an alkyl group containing a heteroatom or a carbonyl group, X is O, NR, S, PR, or $SiR_2$, n=0-2, and m=0 or 1.

Particularly preferred are SiH-functional arylketones wherein Ar is selected from the group consisting of

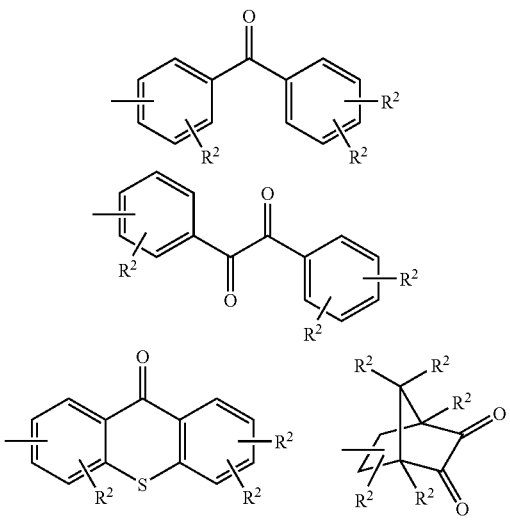

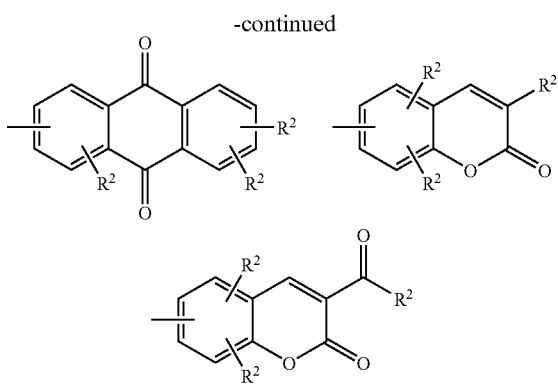

wherein
R² is independently a linear or branched alkyl group, cycloalkyl, alkylenoxy, alkenyl or aryl group, an alkyl group containing a heteroatom, a carbonyl group, H, OR, NR₂, SR, F, Cl, Br or I.

In one preferred embodiment, the precursor which can be used to prepare polymeric benzophenone photoinitiators is a SiH-functional benzophenone derivative having the structure shown in formula IA.

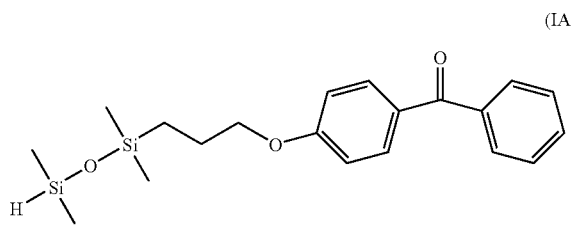

(IA)

In another embodiment of the invention, the precursor which can be used to prepare polymeric thioxanthane photoinitiators is a mercapto-functional thioxanthane derivative having the structure shown in formula IB.

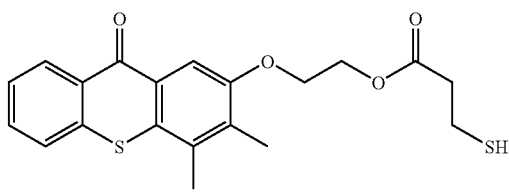

(IB)

Precursor compounds IA and IB of the invention may be prepared as described in Examples 2 and 6, respectively.

The precursor compounds of the invention are grafted to a polymer backbone to form polymer bound Type II photoinitiators. Any polymer with residual unsaturation or that has been maleinized (reacted with maleic anhydride) can be used in the practice of the invention. Unsaturated polymers that can be used in the practice of the invention include but are not limited to styrene-butadiene-styrene (SBS), styrene-isoprene-styrene (SIS), poly(butadiene) (pBD), random styrene-butadiene-styrene rubber (SBR), ethylene-propylene-dicyclopentadiene (EPDM) and acrylate polymers containing pendent or backbone unsaturation. Maleated base polymers include: acrylates, polybutadiene, polyisoprene, SIS, SBS, styrene-b-ethylene/butylene-b-styrene, styrene-b-ethylene/propylene-b-styrene, or polyisobutylene.

One preferred photoinitiator is a siloxane-linked photoinitiator formed by reacting a SiH-functional diaryl ketone with an unsaturated polymer (Q) is represented by the structure:

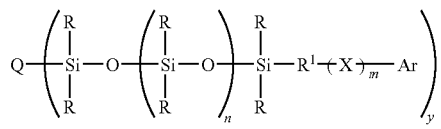

wherein
Ar, is as defined as above,
Q is a small molecule or polymer,
R is independently a linear or branched alkyl group, cycloalkyl, alkylenoxy, alkenyl or aryl group, an alkyl group containing a heteroatom, or H,
R¹ is independently a linear or branched alkyl group, cycloalkyl, alkylenoxy, alkenyl or aryl group, or an alkyl group containing a heteroatom or a carbonyl group,
X is O, NR, S, PR, or SiR₂,
n=0-2,
m=0 or 1, and
y=1-100.

In some systems, type II photoinitiators can participate in crosslinking, in which case y is preferably 2 or more so that it is a multifunctional material.

Preferred sulfide-linked photoinitiators are represented by the following structure:

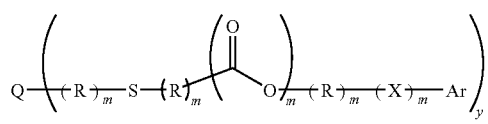

wherein
Q and Ar are as defined above,
R is independently a linear or branched alkyl group, cycloalkyl, alkylenoxy, alkenyl or aryl group, an alkyl group containing a heteroatom or a carbonyl group,
X is O, NR, S, PR, or SiR₂,
m=0 or 1, and
y=1-100.

Preferred amide-linked photoinitiators are represented by the following structure:

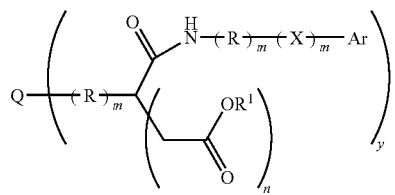

wherein
Q and Ar are as defined above,
R is independently a linear or branched alkyl group, cycloalkyl, alkylenoxy, alkenyl or aryl group, an alkyl group containing a heteroatom or a carbonyl group, $R^1$ is independently a linear or branched alkyl group, cycloalkyl, alkylenoxy, alkenyl or aryl group, an alkyl group containing a heteroatom, a carbonyl group or H.

X is O, NR, S, PR, or $SiR_2$, m=0 or 1, n=0 or 1, and y=1-100.

The presence of the chromophores in the polymeric photoinitiators of the invention renders them sensitive to ultraviolet and/or visible irradiation and thus capable of initiating and/or participating in crosslinking upon exposure to such a source of light.

Polymeric photoinitiators of the invention prepared by bonding the precursor compounds IA and IB to poly(butadiene) are shown in formulas IIA and IIB, respectively.

ultraviolet radiation and ionizing radiation created by the emission of electrons or highly accelerated nuclear particles such as neutrons, alpha-particles etc.

Relative to typical commercially available photoinitiators, the polymeric photoinitiators of the invention are thermally and hydrolytically stable before and after UV cure, exhibit reduced odor after cure in UV curable compositions, exhibit reduced extractables in UV curable compositions, and efficiently UV cure thick films.

Pressure sensitive hot melt adhesive compositions of the type described in, e.g., U.S. Pat. Nos. 4,820,746, 4,948,825, 5,093,406, 5,104,921, 5,115,008, 5,135,978, 5,166,226, 5,302,649, 5,614,577 and 5,804,663 may be prepared using the polymeric photoinitiators of the invention.

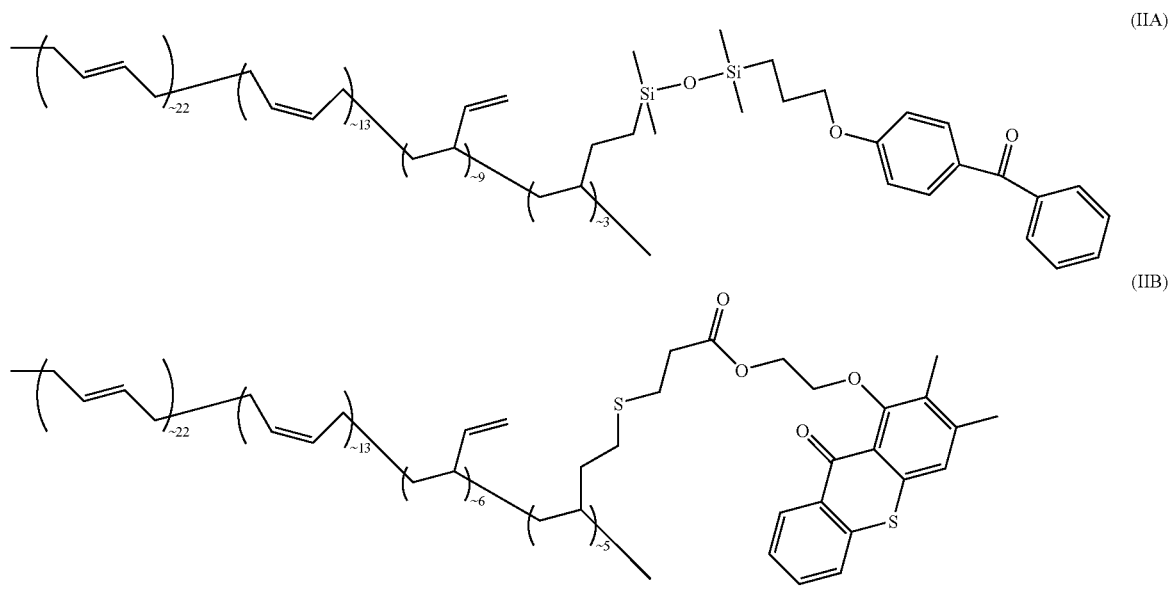

Polymeric photoinitiator compounds IIA and IIB of the invention may be prepared as described in Examples 3 and 7, respectively.

The polymeric photoinitiators of the invention may be used to prepare a wide variety of radiation curable materials including pressure sensitive hot melt adhesives and coating compositions. The use of the term coating compositions is used broadly herein to mean decorative and abrasion resistant coatings, lacquers, fiber reinforced composites, microelectronic encapsulations, die-attach, fiber optic coatings, molding compounds, UV-set structural resins and the like.

Photocurable compositions contemplated for use include compositions comprising a siloxane-linked photoinitiator derived from the reaction of a SiH-functional diarylketone and an unsaturated compound, a sulfide-linked photoinitiator derived from the reaction of a SH-functional diarylketone and an unsaturated compound and/or an amide-linked photoinitiator derived from the reaction of an amino-functional diarylketone and a compound containing either an anhydride or a carboxylic acid functionality. Included are thiol-ene photocurable compositions comprising a multifunctional thiol, a multifunctional olefin, and the photoinitiators.

In a radiation curable compositions, crosslinking occurs by exposure to actinic and/or ionizing radiation. The term "radiation" is used herein to include actinic radiation such as In the practice of the invention, any base resins suitable for use in formulating adhesives and coating compositions, as are well known to those skilled in the art, may be used in the practice of the invention. Useful polymers include amorphous polyolefins, ethylene-containing polymers and rubbery block copolymers, as well as blends thereof. Systems, based on acrylate, epoxide, siloxane, styryloxy, vinyl ether and other monomers, oligomers, or prepolymers such as polyimides and cyanate ester resins and/or polymers and hybrids thereof, may be used. The compositions may be selected from liquid or solid olefinically unsaturated systems, such as acrylates, methacrylates, maleimides, styrenics, maleate esters, fumarate esters, unsaturated polyester resins, alkyl resins, polyisoprene, polybutadiene and thiol-ene compositions. Polymers such polyisoprene or polybutadiene, or their random or block copolymers with styrene may be used with or without partial hydrogenation of the diolefin. To increase reactivity, such polymers with no to full hydrogenation of the diolefin can be acrylated via grafting of maleic anhydride followed by the ring opening reaction with a hydroxy acrylate. Such materials are available under the tradename Ricacryl from Sartomer and from Kuraray Chemical as UC Resins. Functional oligomeric or polymeric resins based on backbone structures such as silicones, polyesters and urethanes, such as acrylate, methacrylate, maleimide or vinyl-terminated resins may also be utilized. Particularly useful rubber-based pressure sensitive hot melt adhesives will preferably contain at least one block derived from a vinyl aromatic monomer and at least one block derived from butadiene or isoprene, such as a tackified mixture of styrene-butadiene-styrene block copolymer and a styrene-butadiene block copolymer or a tackified mixture of styrene-isoprene-styrene block copolymer. It is to be understood that rubber-rubber blends as well as acrylic/rubber blends are encompassed as are acrylic-rubber hybrids (e.g., an acrylic polymer grafted with an ethylene-butylene rubber macromer).

The radiation curable hot melt adhesives used in the practice of the invention may be formulated to be pressure sensitive, semi-pressure sensitive, or non-pressure sensitive. As used herein, the term "pressure-sensitive adhesive" refers to a viscoelastic material which adheres instantaneously to most substrates with the application of slight pressure and remains permanently tacky. A polymer is a pressure-sensitive adhesive within the meaning of the term as used herein if it has the properties of a pressure-sensitive adhesive per se or functions as a pressure-sensitive adhesive by admixture with tackifiers, plasticizers or other additives. A semi-pressure sensitive adhesive is one which temporarily possesses sufficient tack to permanently bond the substrate. After this time the adhesive is still permanently tacky but not enough to create a strong bond. Semi-pressure sensitive adhesives are typically used as regular hot melts. That is the bond is made while the adhesive is still molten. The fact that bondable tack extends through the solidification stage creates the opportunity to bond over a wide process range. One cannot coat these types of adhesives and create a bond with them at a later date as with a true pressure sensitive.

Non-limiting examples of polyolefin polymers useful in the practice of the invention include ethylene copolymer as well as blends thereof. The term ethylene copolymer, as used herein, refers to homopolymers, copolymers and terpolymers of ethylene. Examples of ethylene copolymers include copolymers with one or more polar monomers which can copolymerize with ethylene, such as vinyl acetate or other vinyl esters of monocarboxylic acids, or acrylic or methacrylic acid or their esters with methanol, ethanol or other alcohols. Included are ethylene vinyl acetate, ethylene methyl acrylate, ethylene n-butyl acrylate, ethylene acrylic acid, ethylene methacrylate and mixtures and blends thereof. Other examples include but are not limited to recycled polyethylene teraphthalate and polyethylene, ethylene/α-olefin interpolymers, poly-(butene-1-co-ethylene), atactic polypropylene, low density polyethylene, homogenous linear ethylene/α-olefin copolymers, lower melt index n-butyl acrylate copolymers, ethylene vinyl ester copolymers). Random and block copolymers, as well as blends thereof may be used in the practice of the invention. The polymer component will usually be present in an amount of from about 10% to about 60%, more preferably from about 20% to about 45%, more preferably from about 25% to about 35%.

Rubber based adhesive compositions and coating compositions can be prepared using random and/or block copolymers. Compositions enhanced in accordance with the invention may be styrene-butadiene-styrene, styrene-isoprene-styrene, styrene-butadiene and styrene-isoprene block copolymers or mixture thereof. Preferred radiation curable rubber-based adhesives comprise at least one high vinyl block copolymer. High vinyl block styrene-butadiene-styrene copolymers and/or styrene-isoprene-styrene copolymers are preferred. While radial and linear block copolymers are preferred for use, other block copolymer morphologies can be used as would be recognized by those skilled in the art. The term block copolymers include di-block, tri-block and multi-block copolymers.

A crosslinking agent, in particular a polythiol or poly(maleimide) crosslinking agent, can optionally and desirably be used when formulating rubber-based pressure sensitive adhesives. When formulating rubber based UV curable adhesive compositions, the polythiol is normally present in a concentration of up to about 10% by weight preferably from 0.3 to about 6% by weight more preferably from about 0.3 to about 1% by weight based on a total weight of the pressure-sensitive adhesive rubber and total functional polythiol. A variety of polythiols can be used, including pentaerythritoltetrathiolglycolate, pentaerythritoltetrakis(3-mercaptopropionate), trimethylolethanetrimercaptopropionate, trimethylolpropanetrithioglycolate, trimethylolpropanetris(3-mercaptopropionate) and mixtures thereof.

Radiation curable thiol-ene compositions comprise a polythiol, an olefinic or 'ene' compound, and the polymeric photoinitiator of the invention. The polyene component of the thiolene system may be any component containing a reactive, unsaturated group, most desirably attached to an electron-rich atom or group. Thus, a preferred polyene is a polyfunctional vinyl ether; other suitable groups include but are not limited to allylic ethers; vinyl sulfides; styrenes; acrylamides and acetylenes. Another suitable class of compounds are materials derived from the esterification of a polyol and bicyclic enes such as norbornene carboxylate (the reaction product of cyclopentadiene and acrylate), although their ester functionality may compromise hydrolytic stability. With respect to the thiol (mercaptan) component, primary thiols containing 6 to 40 carbon atoms, such as 1,10-decane dithiol, or any linear, cyclic or branched hydrocarbon thiol containing from one to ten thiol groups may be used. Primary thiols are preferred, inasmuch as they are most reactive, followed by secondary, and, finally, the least reactive tertiary thiols. Examples of useful polythiols include but are not limited to ethylene glycol bis(thioglycolate), ethylene glycol bis(β-mercaptopropionate), trimethylolpropane tris(thioglycolate), trimethylolpropane tris(β-mercaptopropionate), pentaerythritol tetrakis(thioglycolate, pentaerythritol tetrakis(β-mercaptopropionate), all of which are commercially available. In general, one skilled in the art can apply various methods to synthesize polythiols tailored to specific application areas. A particularly useful class of polythiols are derived from the esterification of various polyols with mercapto-acids such as 3-mercaptopropionic acid.

The polymeric photoinitiators of the invention will typically be used in amounts of from about 0.05% by weight to about 10% by weight of the chromophore portion of the polymer based on the weight of the formulated composition, preferably in amounts ranging from about 0.2% by weight to about 3% by weight, more preferably from about 0.5% by weight to about 1.5% by weight. The concentration is chosen based on the thickness of the application of the uncured radiation curable composition. Combinations of two or more photoinitiators may also be used to achieve the best possible cure of the formulated compositions. Photoinitiators are preferably used in the least amount necessary to get initiation of cure at the line speed of the process and desired strength for the end use contemplated. This amount will be dependent on the polymeric composition, as well as the source of radiation, the amount of radiation received, the production line speed, and the thickness of the coating on the substrate. The cure process is generally more efficient in the absence of oxygen, for example, in the presence of nitrogen, so a greater amount of photoinitiator is generally required in the presence of oxygen.

Adhesives and coatings comprising the polymeric photoinitiators of the invention will be formulated with conventional additives known and used by the skilled artisan. The polymer composition may also comprise various other additives chosen based upon the contemplated end use of the polymer. For example, if the end use is a pressure sensitive adhesive, additives such as plasticizers, tackifiers, and fillers, which are conventionally used in the preparation of hot melts and pressure sensitive adhesives can be added. The choice and amount of these additives are within the expertise of those skilled in the art.

Solid hydrogenated tackifying resins are useful in the radiation curable composition of the invention in concentrations ranging from about 30% by weight to about 80% by weight, preferably in amounts ranging from about 45% by weight to about 70%, more preferably from about 50% by weight to about 65% by weight. Representative tackifying resins include the $C_5/C_9$ hydrocarbon resins, synthetic polyterpenes, rosin, rosin esters, natural terpenes, and the like.

Waxes suitable for use in the present invention include paraffin waxes, microcrystalline waxes, high density low molecular weight polyethylene waxes, by-product polyethylene waxes, Fischer-Tropsch waxes, oxidized Fischer-Tropsch waxes and functionalized waxes such as hydroxy stearamide waxes and fatty amide waxes. It is common in the art to use the terminology synthetic high melting point waxes to include high density low molecular weight polyethylene waxes, by-product polyethylene waxes and Fischer-Tropsch waxes. Modified waxes, such as vinyl acetate modified and maleic anhydride modified waxes may also be used. The wax component is utilized at levels of greater than about 10 weight percent, typically about 20 to 40 weight percent, by weight of the adhesive.

The formulated compositions of the present invention may also comprise about 0% by weight to about 40% by weight of an oil diluent. Suitable plasticizing or extending oils include olefin oligomers and low molecular weight polymers as well as vegetable and animal oil and their derivatives. The petroleum derived oils which may be employed are relatively high boiling materials containing only a minor proportion of aromatic hydrocarbons (preferably less than 30% and, more particularly, less than 15% by weight of the oil). Alternatively, the oil may be totally non-aromatic. Suitable oligomers include polypropylenes, polybutenes, hydrogenated polyisoprene, hydrogenated polybutadiene, or the like having average molecular weights between about 350 and about 10,000. Examples include LUMINOL T350, a mineral oil available from Petrocanada and KAYDOL OIL available from Witco Corporation.

Antioxidants are typically added to the commercially available compounds in order to protect the ingredients against degradation during preparation and use of the compositions, however without interfering with the irradiation curing of the polymer. Combinations of antioxidants are often more effective due to the different mechanisms of degradation to which various polymers are subject. Examples of commercially available antioxidants include IRGANOX 1010 (pentaerythrityl-tetrakis[3-(3,5-di-tert-butyl-4-hydroxyphenyl)propionate); IONOL (2,6-di-tertiary-butyl-4-methyl phenol); IONOX 330 (3,4,6-tris(3,5-di-tertiary-butyl-p-hydroxybenzyl)-1,3,5-trimethylbenzene); and POLYGARD HR (tris-(2,4-di-tertiary-butyl-phenyl) phosphite). To ensure long-term thermal stability, in general from about 0.1% to about 3% by weight of one or more antioxidants is included in the adhesive compositions, preferably from about 0.4% by weight to about 1.5% by weight.

In addition to the above-described additional materials, the various compositions of the present invention may include other additives known to those skilled in the art. These additives may include, but are not limited to, pigments, fillers, fluorescent additives, flow and leveling additives, wetting agents, surfactants, antifoaming agents, rheology modifiers, stabilizers, photosensitizers and antioxidants. Preferred additives are those which do not have appreciable absorption in the wavelengths of interest.

Examples of pigments and filler materials include, but are not limited to, titanium dioxide, hydrophobic amorphous fumed silica, amorphous precipitated silica, carbon black, and polymer powders. Examples of flow and leveling additives, wetting agents, and antifoaming agents include silicones, hydrocarbons, fluorine-containing compounds, and non-silicone polymers and copolymers such as copolyacrylates.

The compositions of the invention are prepared by conventional methods. As an example, the block copolymers, the tackifying resin and other desired components may be blended at an elevated temperature, (e.g. temperature of about 300° F.) using an extruder, a Z-blade mixer or other conventional mixing device.

The polymer composition disclosed herein can be used in most applications where an adhesive or coating composition is applied to a backing or substrate. The substrate can be in the form of films, tapes, sheets, panels, and the like, and can be made of materials, such as, paper, fabric, plastic, nonwoven fiber (e.g., disposable absorbent garments), metal, foil, natural rubber, synthetic rubber, wood and wood composites.

Application of the composition of the invention to the substrate may be accomplished using any conventional means, such as, roller, slot orifice, spray or extrusion coating. If a coated substrate is to be used in the form of a roll, the back of the substrate may be coated with a release backsize to prevent the composition from adhering to that side of the substrate. If a substrate is to be coated on both sides and rolled, a release paper or other protective means may be laid on one layer of the composition to prevent that layer from adhering to the composition on the other side of the substrate. In some uses, a second substrate may be applied directly to the composition.

After the polymer composition is applied to the substrate, it is crosslinked by ultraviolet (UV) or electron beam (EB) radiation in air or nitrogen atmospheres. The crosslinking may be done immediately, during or after application of the polymer. The composition containing the photoinitiator is exposed to ultraviolet radiation having a wavelength within the range of 180 to 400 nm, preferably 200 to 390 nm, for a period of time sufficient to accomplish the desired amount of crosslinking. The exact length of exposure will be dependent upon the nature and intensity of the radiation, the particular ultraviolet photoinitiator and amount used, the polymer system, the thickness of the film, environmental factors, and the distance between the radiation source and the adhesive film. The determination of these parameters is within the expertise of one skilled in the art. The actual radiation used can be actinic light from any source, provided it furnishes an effective amount of ultraviolet radiation, since the compositions of the invention activatable by actinic light will generally exhibit their maximum sensitivity to wavelengths in the ultraviolet range. Irradiation may be carried out at any temperature, and most suitably is carried out at room temperature for economic reasons. The distance between the radiation source and adhesive on the coated substrate may range from about 0.32 cm to 25.4 cm (⅛th to 10 inches), and preferably is from 0.32 cm to 17.8 cm (⅛ to 7 inches).

The following examples are provided for illustrative purposes only.

EXAMPLES

Example 1

Synthesis of 4-allyloxybenzophenone (1)

4-hydroxybenzophenone (186.7 g, 940 mmol, Fluka Chemical) was dissolved in 2-butanone (700 mL, Fisher Scientific) in a 2 L four-necked flask equipped with a mechanical stirrer, reflux condenser, addition funnel and internal temperature probe. $K_2CO_3$ (195 g, 1.41 mol, Aldrich Chemical) was added to the reactor, and the contents was placed under a slow $N_2$ purge. Allyl bromide (123 mL, 1.41 mol, Aldrich Chemical) was charged to the addition funnel. The pot temperature was raised to 65° C., at which point the allyl bromide was added over the course of 30 minutes. The reaction was stirred for 6.5 h at 65° C. after the addition was completed. At this point no starting material was present as determined by GC analysis.

The slurry was filtered, and the filtrate was extracted with 1% $HCl_{aq}$ (500 mL). The organic layer was isolated, dried over $MgSO_4$ anhyd., filtered, and solvent removed in vacuo to yield a pale yellow solid (1; 207 g, 92%). The product exhibited acceptable $^1H$ and $^{13}C$ NMR, FT-IR, GC and UV-Vis characteristics.

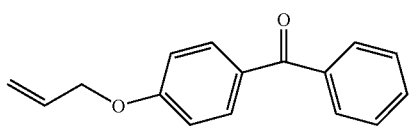

(1)

Example 2

Synthesis of SiH-Functional Benzophenone Derivative (2)

Allyloxybenzophenone 1 (200 g, 840 mmol) was dissolved with warming in THF (150 mL, EM Science) and charged to an addition funnel placed on a 2 L four-necked flask equipped with a mechanical stirrer, reflux condenser and internal temperature probe under a dry air purge. To the reaction vessel was added 1,1,3,3-tetramethyldisiloxane (740 mL, 4.18 mol, Hanse Chemie) and THF (100 mL). The internal pot temperature was raised to 50° C., at which point chlorotris(triphenylphosphine) rhodium ("Wilkinson's catalyst", 22 mg, 11 ppm based on mass of allyloxybenzophenone 1, Aldrich Chemical) was added to the pot along with a portion (5 mL) of the 4-allyloxybenzophenone/THF solution. The internal reaction temperature was raised to 60° C., at which point the 4-allyloxybenzophenone solution was added to the reactor pot over the course of 45 min. The internal temperature of the reaction was held between 60-65° C. during the course of the addition, which is exothermic. After the addition was complete, the reaction was stirred at 60° C. for an additional 15 min., at which point no starting material was present by GC analysis. The reaction was allowed to cool to 35° C., and activated carbon (3 lab scoops, Aldrich Chemical) was added.

The resulting slurry was stirred for 30 min., then filtered to yield a pale yellow solution. Solvent was removed from the product in vacuo to yield a yellow oil (329 g, 104% due to presence of ~10 mol % 1,1,3,3,5,5-hexamethyltrisiloxane in the commercial grade 1,1,3,3-tetramethyldisiloxane starting material; i.e. the reaction is essentially quantitative). The product exhibited acceptable $^1H$, $^{13}C$ and $^{29}Si$ NMR, UV-Vis and FT-IR spectral characteristics.

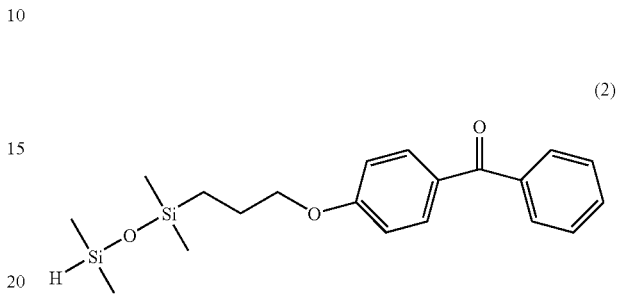

(2)

Example 3

Synthesis of Poly(butadiene)-grafted Benzophenone Polymeric Photoinitiator (3)

Ricon 130 poly(butadiene) (734 g, Sartomer) was solvated in toluene (1100 mL, EM Science) in a 5 L four-necked flask equipped with mechanical stirring, reflux condenser, internal temperature probe, and addition funnel under a purge of dry air. The SiH-functional benzophenone derivative 2 (328.8 g, 0.88 mol) was charged to the addition funnel. A portion of compound 2 (~5 mL) was added to the pBD solution. The solution of pBD was warmed to 50° C., at which point a solution of $Pt^0$ in 1,3,5,7-tetravinyl-1,3,5,7-tetramethylcyclotetrasiloxane (1.8 g 3.0-3.5 wt. % Pt cat. soln, SIT7900.0 from Gelest) was added to the reactor pot. The internal temperature of the reaction was then raised to 80° C., and compound 2 was added dropwise over the course of 1.5 h. An internal temperature between 80-83° C. was maintained throughout the controllably exothermic addition.

After the addition, the final stages of the reaction were followed by FT-IR analysis by monitoring the complete disappearance of the SiH band at 2120 $cm^{-1}$. The SiH moieties were completely consumed after 30 min. at 80° C. It is noted that this time may vary slightly depending on the activity of the $Pt^0$ catalyst solution.

The solution was allowed to cool to 35° C., at which point it was treated with 7 small lab scoops of activated carbon. This slurry was stirred for 60 minutes, then filtered. Solvent was removed from the resulting pale yellow solution in vacuo to yield a viscous pale yellow oil (1060 g, essentially quantitative chemical yield). The product pBD-bound benzophenone derivative 3 exhibited expected $^1H$, $^{13}C$, $^{29}Si$ and FT-IR spectral characteristics. GPC analysis using both RI and UV detectors (λ=320 nm) indicated the vast majority of the benzophenone chromophore was attached to the pBD backbone, and that little pBD MW change had occurred during the grafting process (note a small MW increase may be observed due to the now covalently bound chromophores).

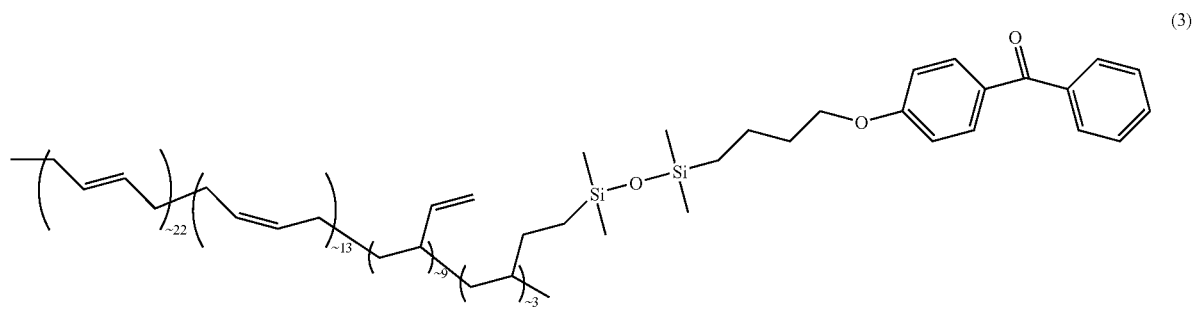

(3)

Example 4

Synthesis of 2-hydroxy-3,4-dimethyl thioxanthone (4)

A solution of 2,2'-dithiobisbenzoic acid (10.0 g, 32.6 mmol, Fluka) in conc. $H_2SO_4$ (100 mL, EM Science) was prepared in a 250 mL three-necked flask equipped with mechanical stirring and an internal temperature probe under $N_2$. This mixture was cooled to 5° C. on an ice bath. To this cooled solution was added 2,3-dimethylphenol (7.98 g, 65.3 mmol, Aldrich Chemical) portionwise over the course of 30 min. No significant exotherm was observed. The reaction was stirred on ice for 1 h, then allowed to warm to room temperature. The reaction was subsequently heated to 65° C. internal temperature for 1 h, then allowed to cool back to room temperature.

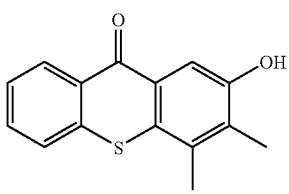

(4)

Example 5

Synthesis of 2-hydroxyethyl-3,4-dimethyl thioxanthone (5)

The hydroxy-functional thioxanthone 5 (0.23 g, 0.8 mmol) was solvated in DMF (11 mL, EM Science) in a 100 mL three-necked flask equipped with mechanical stirring and reflux condenser under $N_2$. To this solution was added 2-bromoethanol (0.06 mL, 0.8 mmol, Aldrich) and $K_2CO_3$ (0.16 g, 1.2 mmol) with stirring. The resulting slurry was heated to 90° C. on an oil batch for 10 h.

The reaction was allowed to cool to room temperature, and poured onto dist. $H_2O$ (150 mL). The slurry was filtered, and the isolated solids were washed thoroughly with distilled water (3×100 mL) and once with isopropanol (20 mL, EM Science). The product was dried in a vacuum oven and analyses by $^1H$ NMR and FT-IR.

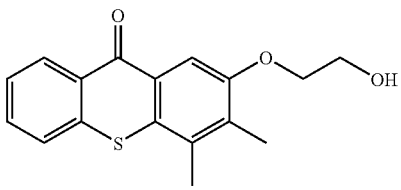

(5)

Example 6

Synthesis of Mercapto-functional Thioxanthone Derivative (6)

The hydroxy-functional thioxanthone 5 can be esterified with 3-mercaptopropionic acid using standard Fisher Esterification protocol. Thus, compound 5 (1 g, 2.9 mmol) can be solvated in toluene (20 mL) in a 50 mL three-necked flask equipped with magnetic stirring and a Dean-Stark condenser under $N_2$. To this solution is added 3-mercaptopropionic acid (0.3 g, 2.9 mmol, Aldrich Chemical) and a catalytic amount of p-toluenesulphonic acid monohydrate (0.006 g, 0.029 mmol, Aldrich Chemical). The resulting solution can be heated to reflux to azeotropically remove water and affect esterification. When water evolution has ceased, the solution is allowed to cool to room temperature and extracted with distilled $H_2O$ (20 mL). The organic layer is isolated, dried over anhyd. $MgSO_4$ (Baker), filtered, and solvent removed in vacuo to produce mercapto-functional thioxanthone 6.

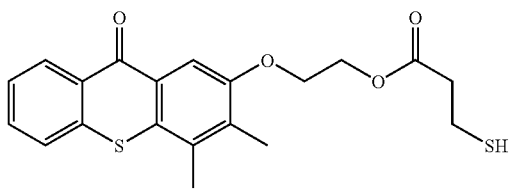

(6)

Example 7

Synthesis of Polymer-bound Thioxanthone Photoinitiator (7)

The mercapto-functional thioxanthone 6 can be grafted onto poly(butadiene) under radical conditions as described in the literature (Schapman, F.; Couvercelle, J. P.; Bunel, C. *Polymer*, 1998, 39(20), 4955-4962.). Thus, Ricon 130 pBD (10 g) can be added to a 100 mL three-necked flask equipped with mechanical stirring and internal temperature probe under $N_2$. Compound 6 (3 g) is added, followed by 2,2'-azobis (2-methylpropionnitrile) ("AIBN", 0.013 g, Aldrich Chemical). The resulting mixture is heated to 75° C. to affect attachment of the thiol groups to the unsaturated rubber and produce the polymer-bound thioxanthone derivative 7.

Example 9

UV Curable Rubber-based PSA Composition, Curing and Evaluation

A rubber-based UV curable pressure sensitive adhesive composition was formulated utilizing the polymeric photoinitiator described in Example 3. SBS block copolymer, SB diblock copolymer, tackifier resins, oil plasticizer, and a typi-

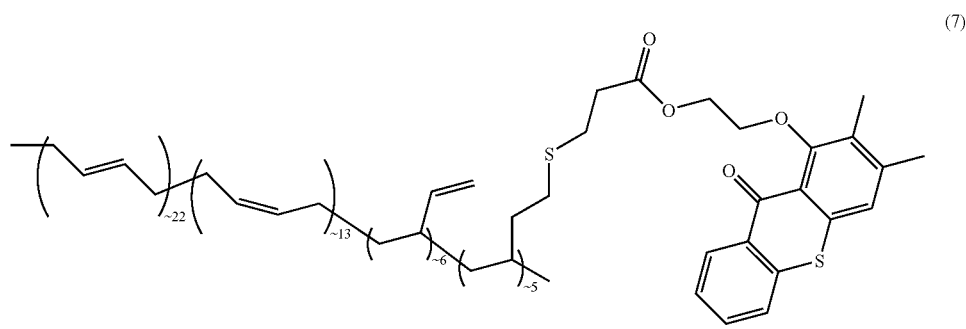

(7)

Example 8

Synthesis of Amide-linked Polymer-bound Photoinitiator (8)

A solution of Ricon 131MA17 (28 g, Sartomer), 4-aminobenzophenone (7.8 g, 39 mmol), and toluene (45 mL) were combined in a 250 mL four-necked flask equipped with a reflux condenser, internal temperature probe, and mechanical stirring under $N_2$. The stirred mixture was heated to 82° C. for 7 h, then the solvent was removed in vacuo to yield the amide-linked polymeric photoinitiator 8 in quantitative yield. The product exhibited acceptable $^1H$, UV-Vis, and FT-IR spectral characteristics.

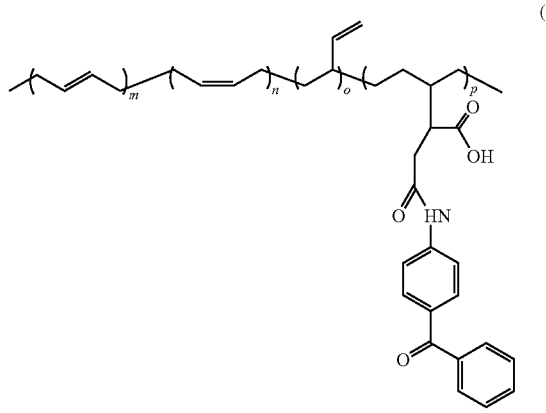

(8)

cal stabilizer package were melt blended with varying amounts of the polymeric photoinitiator at 300° F. Films of various thicknesses were processed from this melt onto release paper, allowed to cool, and cured using a UV Process conveyor line curing unit. The unit was equipped with a 300 W medium pressure mercury arc bulb, and dose was varied by varying the belt speed of the conveyor. Doses were measured with an EIT Power Puck radiometer.

Cured films (and uncured reference samples) were then laminated to Mylar backing substrate (~2 mil substrate thickness). Sample films were cut into a standard geometry for 180° peel and hot shear testing (1"×1" lap bonds for hot shear testing, 1"×6" test strips for peel testing; peel test rate=12"/min.; hot shear conditions were 200° F. with a 500 g mass attached to the sample; all sample preparation was performed under controlled temperature (70° F.) and humidity (50% RH) conditions).

Representative results of these tests are shown in Table 1. From this data several conclusions are clear. All of the samples containing the polymeric photoinitiator are readily UV cured at typical UV doses as evidenced by the increase in hot shear strength upon UV curing. This is a result of the UV induced crosslinking of the systems which increased their cohesive strength to various degrees. Hot shear strength is a standard measure of PSA temperature resistance. The increased temperature resistance of these adhesives allows for their use at temperatures much higher than analogous uncured PSAs. As the adhesives are UV crosslinked, their peel strength decreases relative to the uncured reference sample. The important point with regard to this data is that peel adhesion that is acceptable for many PSA applications can be maintained in a UV cured material while achieving excellent temperature resistance. It is also notable that fairly thick films (5 mils and thicker) of adhesive can be UV cured effectively.

TABLE 1

| wt. % active chromophore | 2% | 1% | 1% | 1% | 2% | 2% | 2% |
|---|---|---|---|---|---|---|---|
| film thickness (mil) | 2 | 2 | 2 | 5 | 2 | 2 | 5 |
| UV Dose (mJ/cm$^2$)[a] | uncured | 1000 | 450 | 1000 | 450 | 1000 | 1000 |
| 180 Peel (lb.)[b] | 4-5 | 3.6 | 3.8 | 4.8 | 3.1 | 2.3 | 2.8 |
| Hot Shear (time)[c] | ~0 | >24 h | 6 min | 38 min | 7 min | >72 h | 16 h |
| Failure Mode | cohesive | cohesive | cohesive | cohesive | cohesive | cohesive | cohesive |

[a] broadband (250 nm-400 nm) UV dose
[b] 1" tape
[c] 200° F., 500 g, 1 in$^2$ lap

Example 10

Use of Polymeric H-abstraction Class Photoinitiators in Thiol-ene UV Crosslinkable Systems A prototypical thiol-ene UV curable composition was formulated utilizing the basic resin components tetraallyl bisphenol A (Bimax), and tetrathiol 10 derived from this base resin. These two components were mixed with a 1:1 thiol:ene molar ratio. This stock resin system was then used to produce three different formulations as given in Table 2 below. Formula (F1) is the resin system with no added photoinitiator, Formula 2 (F2) is the resin system blended with 2 wt. % benzophenone (a typical small molecule photoinitiator), and Formula 3 (F3) is the resin system blended with ca. 8 wt. % of the polymeric photoinitiator of Example 3 (note: 8 wt. % of the polymeric photoinitiator is equivalent to ca. 2 wt. % of pendant benzophenone chromophores). The UV curing behavior of these formulations was evaluated by photodifferential calorimetry (Perkin Elmer DSC-7 equipped with 100 W medium pressure mercury lamp, total light intensity at sample ca. 22 W/cm$^2$). Reactivity was judged by both the enthalpy of polymerization ($\Delta H_p$), the related chemical conversion, and time to maximum polymerization exotherm ($\Delta t_{o-p}$). Results are summarized in Table 2 and in FIG. 1.

TABLE 2

| Formulation | $\Delta H_p$ (J/g) | ~% conversion | $\Delta t_{o-p}$ (seconds) |
|---|---|---|---|
| F1: no photoinitiator | −18 | 6 | 8.4 |
| F2: 2 wt. % benzophenone | −117 | 40 | 7.8 |
| F3: 2 wt. % polymer-bound benzophenone (8 wt. % polymer 3) | −132 | 45 | 7.8 |

As can be seen by comparing formulations 1 and 2 (via Table 2 and FIG. 1), the polymeric photoinitiator 3 performed as well as, if not better than, the typical thiol-ene photoinitiator benzophenone. Specifically, the thermodynamic quantities of enthalpy of polymerization/chemical conversions were essentially the same. Also, the time to peak exotherm, a qualitative measure of photopolymerization kinetics, was similar for both systems. As can be seen from formulation 1, this thiol-ene system has trace UV sensitivity even in the absence of any discrete photoinitiator. This frequent "initiator-free" activity of thiol-ene systems has been previously ascribed to the formation of ground or excited state charge transfer complexes or simply the photogeneration of low levels of radical initiators via various routes. For the purposes of this invention, the key items of interest are the facts that 1) the systems that incorporated added photoinitiators are orders of magnitude more reactive than the one that did not, and 2) the polymeric photoinitiator 3 exhibits essentially equal reactivity as the small molecule photoinitiator benzophenone.

Example 11

Further Use of Polymeric H-abstraction Class Photoinitiators in Thiol-ene UV Crosslinkable Systems (Filtered Analyses)

A prototypical thiol-ene UV curable composition was formulated utilizing the basic resin components of pentaerythritoltetrakis(3-mercaptopropianate) (Hampshire Chemical), and triallylisocyanurate (Aldrich, ~200 ppm BHT stabilizer). These two components were mixed with a 1:1 thiol:ene molar ratio. This stock resin system was then used to produce two formulations as given in Table 3 below. Formula (F1) is the resin system with no added photoinitiator, Formula 2 (F2) is the resin system blended with 8 wt. % of the polymeric photoinitiator of Example 3 (note: 8 wt. % of the polymeric photoinitiator is equivalent to ca. 2 wt. % of pendant benzophenone chromophore). The UV curing behavior of these formulations was evaluated by photodifferential calorimetry (Perkin Elmer DSC-7 equipped with 100 W medium pressure mercury lamp, total light intensity at sample ca. 22 mW/cm$^2$). Reactivity was judged by both the enthalpy of polymerization ($\Delta H_p$), the related chemical conversion, and time to maximum polymerization exotherm ($\Delta t_{o-p}$).

It is known to those skilled in the art that certain thiol-ene formulations exhibit significant photoreactivity without added photoinitiator. This formulation without added photoinitiator (F1), if irradiated with unfiltered UV light with the spectral distribution of a medium pressure mercury arc lamp does, indeed, show such "initiator-free" activity. In this experiment, the light from the mercury arc lamp was filtered with an interference filter with a ~300 nm cutoff wavelength (i.e. light of wavelengths less than 300 nm are completely filtered). Results of the photoDSC experiments with a 300 nm cutoff filter are shown in Table 3 and FIG. 2. As can be seen from the enthalpy of reaction and conversion of F1 when irradiated with filtered light, minimal reactivity is observed. This is in contrast to the same initiator-free formulation (F1) irradiated with unfiltered light, which exhibits significant conversion. This unfiltered reactivity data is included in Table 3 under the heading "unfiltered reference F1". As can be clearly seen from the data on formulation F2, the polymeric photoinitiator of Example 3 is an efficient initiator for this system, even in the presence of the cutoff filter. This example also clearly shows that the bulk of this reactivity is due to the photoinitiating capability of the polymeric photoinitiator, as opposed to the inherent photoactivity of this particular thiol-ene formulation. Note that the theoretical enthlapies of reaction (for 100% conversion) for F1 and F2 are different due to the different concentrations of thiol and ene in the two formulations that results from incorporation of the polymeric photoinitiator at significant mass levels (8 wt. %). Conversely, the calculated conversion takes this into account. The significant initiator-free activity of this particular thiol-ene system is notable, but not useful if longer wavelengths are used for UV curing (for example, curing through borosilicate glass). In such cases, initiators such as the polymeric one utilized in this example are needed.

TABLE 3

| Formulation | $\Delta H_p$ (J/g) | ~% conversion | $\Delta t_{o-p}$ (seconds) |
|---|---|---|---|
| F1: no photoinitiator | <−63 | 21 | 6.6 |
| F2: 2 wt. % polymer-bound benzophenone (8 wt. % polymer 3) | −182 | 69 | 9.0 |
| unfiltered reference F1 | −244 | 79 | 6.0 |

Example 12

Use of Hydrogen Sources as Coinitiators with Polymeric H-abstraction Class Photoinitiators A stock rubber-based UV curable hot melt pressure sensitive adhesive (UVHMPSA) formulation was prepared using the basic components SBS rubber, hydrogenated tackifiers, saturated oil, and an antioxidant package. To form sample #1, 100 g of this stock PSA was blended with 9 g of the amide-linked polymeric photoinitiator 8 (ca. 2 wt. % active amidobenzophenone chromophore). To form sample #2 a second 100 g portion of the stock PSA was added to 4.5 g of photoinitiator 8 and 1 g of a high MW, low odor polythiol crosslinker (ca. 1 wt. % active amidobenzophenone chromophore and ca. 1 wt. % polythiol crosslinker). Both samples were successfully prepared by both solution and melt processing.

Films of both samples (nominally 2 mil dried film thickness) were drawn from toluene solution. Both samples were cured with a total UV dose of 500 mJ/cm$^2$ on a UVProcess conveyor line (dose represents total does in the UVA, B, C, and V regions of the spectrum as measured by a UVProcess compact radiometer).

Dynamic Mechanical Analysis of both samples indicated that only sample #2, which contained the polythiol H-donor/crosslinker had cured efficiently. This was evidenced by the fact that the rubbery plateau region of UV cured sample #2 extended above 150° C., well over the $T_g$ of the styrene endblocks of the base rubber. Sample #1, which did not cure efficiently, exhibited a drastic reduction in elastic modulus (E') and flow at temperatures above the styrene endblock $T_g$ of ~110° C. It should be noted that, in other rubber-based UVHMPSA systems, photoinitiator 8 does produce effective levels of crosslinking without an additional hydrogen donor/crosslinker.

Thus, in well designed formulations, the use of H-donors/crosslinkers such as polythiols and amines can accelerate the rate and extent of UV cure in systems incorporating the polymeric photoinitiators of the current invention.

Example 13A-C

Use of Polymer-Bound PI in SIS-based Systems

Although it is known that SIS-based pressure sensitive adhesives can be crosslinked with photoinitiators, the UV dose required is excessive unless multifunctional coupling agents are employed such as di-, tri, and tetra-functional acrylates (D. J. St. Clair, Adhesives Age, March 1980, p. 30). However, and as noted by St. Clair, these formulas are not thermally stable and thus are not suitable for use in conventional hot melt processes where manufacture of the adhesive itself will ordinarily expose it to several hours of high temperatures. In general, hot melts should show only minor property changes over 24 hours at their application temperature. For instance, a viscosity change of less than 25% is desirable.

Examples 13A is a comparative example of a SIS block copolymer crosslinked with a convention photoinitiator (Irgacure 819). Example 13B and Example 13C exemplify SIS block copolymers crosslinked with a photoinitiator of the invention.

In these examples, tangent delta was measured using the following procedure:

A Rheometrics Dynamic Mechanical Analyzer (Model RDA 700) was used to obtain the elastic (G') and loss (G") moduli versus temperature. The instrument was controlled by Rhios software version 4.3.2. Parallel plates 8 mm in diameter and separated by a gap of about 2 mm were used. The sample was loaded and then cooled to about −100° C. and the test started. The program test increased the temperature at 5° C. intervals followed by a soak time at each temperature of 10 seconds. The convection oven containing the sample was flushed continuously with nitrogen. The frequency was maintained at 10 rad/s. The initial strain at the start of the test was 0.05% (at the outer edge of the plates). An autostrain option in the software was used to maintain an accurately measurable torque throughout the test. The option was configured such that the maximum applied strain allowed by the software was 50%. The autostrain program adjusted the strain at each temperature increment if warranted using the following procedure. If the torque was below 200 g-cm the strain was increased by 25% of the current value. If the torque was above 1200 g-cm it was decreased by 25% of the current value. At torques between 200 and 1200 g-cm no change in strain was made at that temperature increment. The shear storage or elastic modulus (G') and the shear loss modulus (G") are calculated by the software from the torque and strain data. Their ratio, G"/G', also known as the tan delta, was calculated.

Example 13A

Comparative Example

A pressure sensitive adhesive was formulated based on 20 parts of SIS block copolymer containing 4 parts of Quintac 3530 (available from Nippon-Zeon), 4 parts of Kraton 1119 (available from Kraton Polymers) and 12 parts of Vector 4411 (available from Dexco Polymers), 53 parts of tackifying resin (Escorez 5320, available from Exxon-Mobil Chemical Co.), 23 parts of Britol 35T (a white mineral oil available from Crompton), 0.6 parts of anti-oxidant (0.3 parts Irganox available from Ciba-Geigy and 0.3 Sumilizer TPD available from Sumitomo), 5 parts of multifunctional coupling agent (SR454 triethoxylated trimethylol propane triacrylate) and 1 part of Irgacure 819 (phosphine oxide photoinitiator available from Ciba-Geigy).

The sample was coated at 5 mils on release paper and cured under a Fusion UV H bulb with a dose of 1000 mJ/cm2 of UVB.

Gel fraction in cyclohexane was determined by weighing the cured film, immersing it in a container of cyclohexane overnight, removing the swollen film in the morning and drying. Gel fraction was 21.8% or 87% of theoretical (20% polymer plus 5% multifunctional coupling agent). Uncured films dissolve completely in cyclohexane.

RDA was conducted. Cured films exhibit tangent delta values well below 1.0, preferably below 0.5, and most preferably below 0.2 at high temperatures, i.e., beyond the styrene block Tg. Values are recorded at 160-200° C., where the adhesive would be highly fluid if not for crosslinking. Fluid materials exhibit more viscous behavior and thus higher tangent delta values.

At tangent delta=1 the fluid is behaving equally viscously (fluid like) and elastically (solid like).

The lower the value the more solid-like the behavior.

The tangent delta value of this adhesive was 0.06 at 170° C.

The viscosity of this adhesive was 2,645 cP at 275° F. Viscosity increased linearly with time by 50% over 24 hours.

Example 13B

Inventive Example of SIS-based PSA

A pressure-sensitive adhesive was formulated based on 20 parts of SIS block copolymer (Kraton 1320 available from Kraton Polymers), 53 parts of tackifying resin (Escorez 5400, available from Exxon-Mobil Chemical Co.), 22 parts of Britol, 0.6 parts of anti-oxidant (0.3 parts Irganox 3052 and 0.3 parts Sumilizer TPD) and 4 parts of the photoinitiator described in Example 3.

The adhesive was coated and UV cured as described in the above Example 13A. Tan delta at 170° C. was 0.1 indicating it was well cured.

Example 13C

Inventive Example of SIS-based PSA

A pressure-sensitive adhesive was formulated based on 25 parts of SIS block copolymer (Kraton 1320 available from Kraton Polymers), 53 parts of tackifying resin (Escorez 5400), 18 parts of Britol 35T, 0.6 parts of anti-oxidant (0.3 Irganox 3052 available from Ciba-Geigy and 0.3 Sumilizer TPD available from Sumitomo) and 4 parts of the photoinitiator described in Example 3.

The adhesive was coated and UV cured as described in the above Example 13A. Tan delta at 170° C. was 0.03 indicating it was well cured.

Viscosity of this adhesive at 325° F. is 8575 cP. When held at this temperature it dropped slowly by only 10% in 24 hours. A drop in viscosity upon aging at elevated temperature is typical of SIS-based PSA's due to slow oxidative chain scission. The slight decrease in viscosity is expected and indicates no tendency of the inventive photoinitiator to lead to premature adhesive gelation when heated.

Example 14

Comparison of Photoinitiators of Invention with Conventional Photoinitiators

Conventional photoinitiators (Irgacure 651 and benzophenone) and the photoinitiator of Example 3 were used to crosslink various styrenic block copolymers. Films were prepared using the block copolymers shown in Table 3, a photoinitiator and oil. All block copolymers were obtained from Kraton Polymers. In Table 4, vinyl indicates pendant double bonds, i.e., 1,2 (SBS) or 3,4 (SIS), polymerization.

TABLE 4

|  | high vinyl SBS (Kraton D1192) | SBS (Kraton D1101) | SIS (Kraton D1165) |
| --- | --- | --- | --- |
| % vinyl | 40 | 10 | 12 |
| % styrene | 30 | 30 | 30 |
| % diblock | <1 | 16 | 16 |
| MW (GPC) | 140,000 | 172,000 | 140,000 |

The block copolymer was used at 50 wt. %.

Irgacure 651 (available from Ciba-Geigy) was used at 0.0039 moles/100 g of solids (1 wt. %). This a standard cleavage type photoinitiator that is known to crosslink high vinyl SBS (see U.S. Pat. No. 6,486,229 B1).

Benzophenone (available from Ciba-Geigy) was used at 0.0039 moles/100 g of solids (0.71 wt. %). Benzophenone is a standard non-cleavage photoinitiator.

The photoinitiator of Example 3 was used at 0.0031 equivalents/100 g of active benzophenone sites on the polymeric photoinitiator (3.69 wt. %).

Oil (Britol 35T), the remainder, was used at 46.31 to 49% by weight of the solid composition.

These solid ingredients were dissolved into toluene at 50% solids and the homogeneous solutions were used to cast films onto release liner. These were dried at 250° F. for 3 minutes to produce 2 mil dry films. These were cured as above and then tested by RDA (as described above) and for gel fraction.

Tables 5 reports the gel fraction of the polymer after cure. Table 6 reports the tan delta after cure.

TABLE 5

|  | high-vinyl SBS | SBS | SIS |
| --- | --- | --- | --- |
| Irgacure 651 | 47% | 63% | — |
| Benzophenone | — | 13% | — |
| Example 3 | 97% | 97% | 94% |

TABLE 6

|  | high-vinyl SBS | SBS | SIS |
| --- | --- | --- | --- |
| Irgacure 651 | 0.27 | 0.25 | 7.6 |
| Benzophenone | 0.79 | 0.90 | 8.4 |
| Example 3 | 0.09 | 0.06 | 0.12 |

It is evident from Tables 5 and 6 that the photoinitiator of Example 3 is more effective than conventional photoinitiators in curing all of these styrenic block copolymers and is the only one capable of curing SIS.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

The invention claimed is:

1. An amide-linked photoinitiator having the following structure:

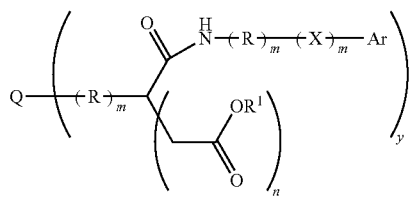

wherein

Q is a small molecule or polymer,

Ar is selected from the group consisting of:

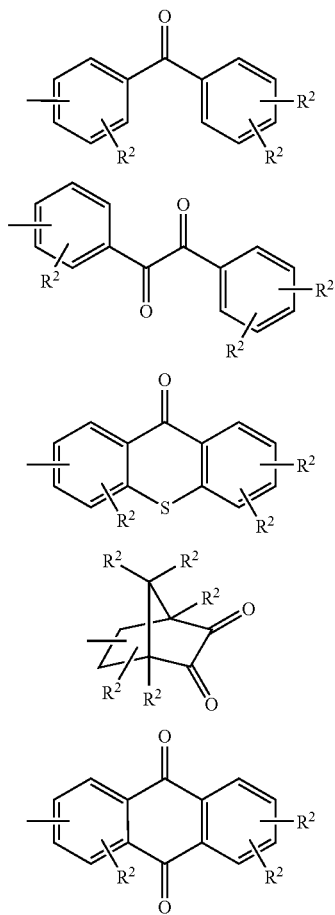

-continued

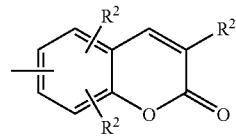

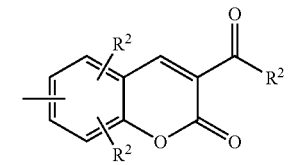

R is independently a linear or branched alkyl group, cycloalkyl, alkylenoxy, alkenyl or aryl group, an alkyl group containing a heteroatom or a carbonyl group, $R^1$ is independently a linear or branched alkyl group, cycloalkyl, alkylenoxy, alkenyl or aryl group, an alkyl group containing a heteroatom, a carbonyl group or H, $R^2$ is independently linear or branched alkyl group, cycloalkyl, alkylenoxy, alkenyl or aryl group, an alkyl groups containing a heteroatom, a carbonyl group, H, OR, $NR_2$, SR, F, Cl, Br or I, X is O, NR, S, PR, or $SiR_2$, m=0 or 1, n=1, and y=1-100.

2. The amide-linked photoinitiator of claim 1 where Q is derived from maleinized poly(butadiene), maleinized poly(isoprene), maleinized poly(styrene-b-butadiene-b-styrene), or maleinized poly(styrene-b-isoprene-styrene), maleinized poly(styrene-b-ethylene/butylene-b-styrene), maleinized poly(styrene-b-ethylene/propylene-b-styrene) or an anhydride functional acrylic polymer.

3. A photocurable composition comprising the photoinitiator of claim 1.

4. The photocurable composition of claim 3 which is a pressure sensitive adhesive.

5. A thiol-ene photocurable composition comprising a multifunctional thiol, a multifunctional olefin, and a photoinitiator claim 1.

6. The amide-linked photoinitiator of claim 1 where m is 1.

7. The amide-linked photoinitiator of claim 1 where Q is derived from styrene-butadiene-styrene (SBS); styrene-isoprene-styrene (SIS); poly(butadiene); random styrene-butadiene-styrene rubber (SBR); acrylate polymers containing pendant or backbone unsaturation; maleinized poly(butadiene), maleinized poly(isoprene), maleinized poly(styrene-b-butadiene-b-styrene), or maleinized poly(styrene-b-isoprene-styrene), maleinized poly(styrene-b-ethylene/butylene-b-styrene), maleinized poly(styrene-b-ethylene/propylene-b-styrene) or an anhydride functional acrylic polymer.

8. The amide-linked photoinitiator of claim 1 where m is 0; $R^1$ is H and Q is derived from maleinized poly(butadiene), maleinized poly(isoprene), maleinized poly(styrene-b-ethylene/butylene-b-styrene), and maleinized poly(styrene-b-ethylene/propylene-b-styrene).

9. The amide-linked photoinitiator of claim 1 where m is 0; and R¹ is H.

10. The amide-linked photoinitiator of claim 1 where m is 0; R¹ is H and Q is derived from styrene-butadiene-styrene (SBS); styrene-isoprene-styrene (SIS); poly(butadiene); random styrene-butadiene-styrene rubber (SBR); acrylate polymers containing pendant or backbone unsaturation; maleinized poly(butadiene), maleinized poly(isoprene), maleinized poly(styrene-b-butadiene-b-styrene), or maleinized poly(styrene-b-isoprene-styrene), maleinized poly(styrene-b-ethylene/butylene-b-styrene), maleinized poly(styrene-b-ethylene/propylene-b-styrene) or an anhydride functional acrylic polymer.

11. The amide-linked photoinitiator of claim 1 where Ar is a benzophenone derivative.

\* \* \* \* \*